(12) United States Patent
Zhang et al.

(10) Patent No.: US 12,714,869 B2
(45) Date of Patent: Aug. 25, 2026

(54) AUTOMATED EXTERNAL DEFIBRILLATOR SYSTEM

(71) Applicant: Everest Acquisition Entity, LLC, Wilmington, DE (US)

(72) Inventors: Yuning Zhang, Shanghai (CN); Xin Ge, Shanghai (CN)

(73) Assignee: Everest Acquisition Entity, LLC, Wilmington, DE (US)

( * ) Notice: Subject to any disclaimer, the term of this patent is extended or adjusted under 35 U.S.C. 154(b) by 193 days.

(21) Appl. No.: 18/291,248

(22) PCT Filed: Jul. 21, 2022

(86) PCT No.: PCT/EP2022/070447
§ 371 (c)(1),
(2) Date: Jan. 23, 2024

(87) PCT Pub. No.: WO2023/001945
PCT Pub. Date: Jan. 26, 2023

(65) Prior Publication Data

US 2025/0099773 A1 Mar. 27, 2025

(30) Foreign Application Priority Data

Jul. 23, 2021 (WO) ................ PCT/CN2021/108161
Sep. 29, 2021 (EP) .................................... 21199701

(51) Int. Cl.
*A61N 1/39* (2006.01)
*A61N 1/362* (2006.01)
(Continued)

(52) U.S. Cl.
CPC ......... *A61N 1/3904* (2017.08); *A61N 1/3625* (2013.01); *A61N 1/365* (2013.01); *A61N 1/37* (2013.01); *G16H 40/63* (2018.01)

(58) Field of Classification Search
CPC ............ A61N 1/37258; A61N 1/37282; A61N 1/3904; A61N 1/39044; A61N 1/3625; A61N 1/3987
See application file for complete search history.

(56) References Cited

U.S. PATENT DOCUMENTS 4,983,079 A 1/1991 Imanaga
2016/0180044 A1 6/2016 Delisle
(Continued)

FOREIGN PATENT DOCUMENTS

JP 2016187437 A 11/2016
KR 101622762 B1 5/2016

OTHER PUBLICATIONS

International Search Report for PCT/EP2022/070447 filed Jul. 21, 2022.

*Primary Examiner* — George R Evanisko
(74) *Attorney, Agent, or Firm* — Bond, Schoeneck & King, PLLC

(57) ABSTRACT

Provided is an Automated External Defibrillator AED and a server. The AED makes an ECG measurement of a heart and transmits the measurement to a remote processing device, for example the server, and receives back from the server a first classification of the ECG measurement. The AED also performs a local analysis of the ECG measurement to determine a second classification of the ECG measurement. The AED determines whether to administer a shock/instruct a user to administer a shock based on the first and second classifications.

8 Claims, 7 Drawing Sheets

(51) Int. Cl.

| | |
|---|---|
| ***A61N 1/365*** | (2006.01) |
| ***A61N 1/37*** | (2006.01) |
| ***G16H 40/63*** | (2018.01) |

(56) References Cited

U.S. PATENT DOCUMENTS

| | | | | |
|---|---|---|---|---|
| 2018/0001100 | A1 | 1/2018 | Gehman | |
| 2018/0154163 | A1 | 6/2018 | Amann | |
| 2019/0216350 | A1* | 7/2019 | Sullivan | A61B 5/7267 |
| 2020/0085333 | A1 | 3/2020 | Freed | |
| 2020/0215346 | A1 | 7/2020 | Sturman | |
| 2021/0093876 | A1 | 4/2021 | Montague | |
| 2021/0121090 | A1 | 4/2021 | Weinstein | |

* cited by examiner

AUTOMATED EXTERNAL DEFIBRILLATOR SYSTEM

This application is a national stage application under 35 U.S.C. § 371 of International Application No. PCT/EP2022/070447 filed on Jul. 21, 2022 and published in the English language on Jan. 26, 2023 as International Publication No. WO2023/001945, which claims priority to European Patent Application No. 21199701 filed on Sep. 29, 2021, and International Application No. PCT/CN2021/108161, filed on Jul. 23, 2021, the entire disclosures of which are incorporated herein by reference.

FIELD OF THE INVENTION

This invention related to automated external defibrillators.

BACKGROUND OF THE INVENTION

Automated external defibrillators, also known as AEDs, can typically be found in public spaces like train stations. They are intended to be used by untrained members of the public who cannot reasonably be expected to know when defibrillation is or is not required. To help ensure that subjects are only defibrillated when it is actually required, AEDs typically include an electrocardiogram ECG sensor to measure a subject's heart, and on-board hardware for analyzing the ECG measurement and determining whether a defibrillation shock is required.

Analysis of the ECG measurements is typically carried out using a shock advice algorithm (SAA). In order to improve their accuracy, SAAs have become increasingly complex and resource intensive over time. AEDs are normally battery powered devices that can only supply a limited amount of electrical power, the majority of which is used for defibrillation. Due to this limited electrical supply, the computing chips in AEDs are normally low-power chips, able to operate on a small electrical supply. However, these low-power chips also have limited computational resources. While the computer chips built in to AEDs can perform any mathematical operation, and so could hypothetically be reprogrammed to use new SAAs, they lack the performance required to analyze ECG measurements using advanced SAAs (such as those based in deep neural networks).

EP3204881A1 discloses a system and method for medical premonitory event estimation includes one or more processors to perform operations comprising: acquiring a first set of physiological information of a subject, and a second set of physiological information of the subject received during a second period of time; calculating first and second risk scores associated with estimating a risk of a potential cardiac arrhythmia event for the subject based on applying the first and second sets of physiological information to one or more machine learning classifier models, providing at least the first and second risk scores associated with the potential cardiac arrhythmia event as a time changing series of risk scores, and classifying the first and second risk scores associated with estimating the risk of the potential cardiac arrhythmia event for the subject based on the one or more thresholds.

US2021121090A1 discloses systems, devices and methods for arrhythmia monitoring with a trained classifier including at least one neural network. In some embodiments, an external heart monitoring device may include a plurality ECG electrodes to sense surface ECG activity, ECG processing circuitry to process the surface ECG activity to provide at least one ECG signal, a non-transitory computer-readable medium comprising a rhythm change classifier comprising at least one neural network, and at least one processor to receive the ECG signal(s), detect with the rhythm change classifier time data corresponding to a predetermined rhythm change in the ECG signal(s), determine based on the detected time data at least one ECG signal portion corresponding to the predetermined rhythm change, and transmit the at least one determined ECG signal portion to a remote computer system.

US2020085333A1 discloses a variety of convolutional neural network based shockable heart rhythm classifiers. The neural network is configured to receive an electrocardiogram segment as an input and to generate an output indicative of whether the received electrocardiogram segment represents a heart rhythm that is suitable for treatment by a defibrillation shock. Preferably, the received electrocardiogram segment is not transformed or processed prior to its reception by the convolutional neural network and no features of the electrocardiogram are identified to the convolutional neural network. In some embodiments, the received electrocardiogram segment is the sole input to the convolutional neural network. The described classifier is well suited for use in defibrillators.

US20180154163A1 discloses a system which includes a first computing device comprising a processor coupled to a memory. The processor and the memory are configured to receive at least one of (i) information indicative of treatment of a victim by a first caregiver using the first computing device and (ii) information indicative of a health status of the victim; determine that treatment of the victim by the first caregiver using the first computing device is completed; and transmit the received information to a second computing device.

There is therefore a need for an AED that is capable of exploiting advanced SAAs to analyze ECG measurements quickly and efficiently.

SUMMARY OF THE INVENTION

The invention is defined by the claims.

According to examples in accordance with an aspect of the invention, there is provided an automated external defibrillator comprising:

- a defibrillation module, configured to administer a defibrillation shock;
- a sensor, configured to make an electrocardiogram, ECG, measurement of a heart;
- a connectivity module, configured to communicate with a remote processing device to transmit the ECG measurement and receive a first classification of the ECG measurement; and
- a processor configured to:
  - determine, using a local shock advice algorithm, SAA, a second classification of the ECG measurement, wherein the second classification is selected from a second list comprising at least a shockable classification and a non-shockable classification; and
  - if at least one of the first classification and the second classification of the ECG measurement is a shockable classification, either:
    - cause the defibrillation module to administer the defibrillation shock; or
    - advise a user to administer the defibrillation shock.

The AED makes an ECG measurement of a subject's heart, and transmits the ECG measurement to a remote processing device. The AED subsequently receives, from the remote processing device, a first classification of the ECG measurement. If the ECG measurement is classified as shockable, the AED administers a defibrillation shock or advises the user to administer a defibrillation shock.

The second classification may be obtained before or after the first classification.

The invention separates the classification of the ECG measurement from the AED. In order to improve sensitivity and specificity, the algorithms used to classify ECG measurements (known as shock advice algorithms, SAAs) are becoming increasingly complex and require more computational power to evaluate. It is challenging to implement advanced SAAs using the hardware found in an AED for a number of reasons. Typically, AEDs are built with computer chips that are able to operate from the limited battery power that an AED can provide. While these AEDs could in theory be reprogrammed to use newer SAAs (such as those utilizing neural networks), they would struggle to take advantage of the newer SAAs due to the increased computational requirements of said new SAAs. Evaluating a neural network typically requires a high end computing chip such as a GPU or ASIC, however, these chips require more electrical power than the battery of the AED can provide.

The inventors have realized that the shortcomings of current AEDs can be overcome by creating an internet of things connected AED that transmits ECG measurements to a remote processing device, for example a cloud server. By utilizing a cloud server to classify ECG measurements instead of relying solely on the hardware of the AED, the limitations of the AED no longer prevent the most advanced SAAs from being used. By using better SAAs to classify ECG measurements, the AED can better differentiate between subjects that do or do not require defibrillation. A single remote processing device may be used to classify ECG measurements from multiple AEDs. Should any hardware upgrades be required in order to use new SAAs, a small number of remote processing device can be upgraded instead of needing to upgrade the hardware of many geographically dispersed AEDs.

Although newer SAAs are more accurate in their classification of ECG measurements, it is still useful for the AED to be able to classify an ECG measurement independently, using a less advanced SAA that can be run on the AED's hardware. When a subject experiences ventricular fibrillation, it is important to be able to administer a defibrillation shock to them as quickly as possible in order to maximize their chance of survival. Any network delay that increases the time taken for a defibrillation shock to be delivered decreases the likelihood that the individual will live. Therefore, it is important that the AED can process an ECG signal independently of the remote processing device, so that it can quickly deliver a defibrillation shock when it is needed.

The second list may also include an uncertain classification. When the AED classifies the ECG measurement as non-shockable (or optionally as uncertain), the superior sensitivity and specificity of classification performed by the remote processing device can be used to confirm or overrule the AED's classification. If the remote processing device's classification of the ECG measurement is that it is shockable, the AED will administer a defibrillation shock (or instruct the user to administer a defibrillation shock), notwithstanding the AED's uncertain or non-shockable classification of the ECG. Consequently, fewer patients who require defibrillation will fail to receive defibrillation due to the limitations of the AED.

The connectivity module of the AED may transmit the ECG measurement to the remote processing device before the AED determines the second classification of the ECG measurement.

This can minimize the amount of time between the AED making an ECG measurement and receiving the remote processing device's classification of the ECG measurement. This is particularly beneficial in the case that the AED classifies the ECG measurement as non-shockable or uncertain, because if the remote processing device classifies the ECG measurement as shockable then the defibrillation can be administered more quickly than if transmission of the ECG occurred after the classification performed by the AED.

The connectivity module may instead only transmit the ECG measurement to the server if the second classification of the ECG measurement is the uncertain classification. Thus, the second classification is then obtained first.

This minimizes the amount of time between the AED both making and classifying the ECG measurement. This is can particularly useful in the case that the AED classifies the ECG measurement as shockable, as it may be faster to analyze the ECG measurement locally than to transmit the ECG measurement to the remote processing device and wait to receive the first classification of the ECG. Where the second classification is shockable, the AED can administer a defibrillation shock more quickly than if it had waited for the first classification. Furthermore, by transmitting the ECG to the remote processing device only when the AED classifies the ECG measurement is uncertain, the computational resources of the remote processing device are not wasted by classifying an ECG measurement that the AED has already determined is shockable and for which a defibrillation will be administered or instructed. Although the first classification of the ECG will be more accurate than the second classification, in most cases where the second classification is shockable, the first classification will also be shockable. Similarly, in most cases that second classification is non-shockable, the first classification will also be non-shockable.

The connectivity module may transmit the ECG measurement to the remote processing device if the second classification of the ECG measurement is non-shockable, and optionally also if it is uncertain.

In addition to the benefits of transmitting the ECG measurement to the remote processing device when the AED classifies the ECG as uncertain, transmitting the ECG measurement when the AED classifies the ECG as non-shockable allows the remote processing device to confirm or overrule the AED's classification of the ECG measurement. This can reduce the number of subjects who have a shockable heart rhythm but, without the present invention, would not receive a defibrillation shock because the AED is not able to accurately classify the ECG measurement. The AED may only classify the ECG measurement as shockable or non-shockable, and may not include an uncertain classification.

The connectivity module may communicate wirelessly with the remote processing device to transmit ECG measurements and receive first classifications. This may be achieved using Wifi and/or cell networks such as 3G, 4G, 5G and/or NBIoT. It may be beneficial for the connectivity module to be capable of using more than one of, or all of, these networks so that if one network is unavailable another can be used as a backup.

According to examples in accordance with an aspect of the invention, there is also provided a server, comprising:

a connectivity unit configured to:

receive, from each of one or more automated external defibrillators, AEDs, an electrocardiogram, ECG, measurement;

transmit a first classification of the ECG measurement to the respective AED;

a memory configured to store a definition of a shock advice algorithm, SAA; and processing hardware configured to determine, using the SAA, the first classification of the ECG measurement, wherein the first classification is selected from a list comprising at least a shockable classification and a non-shockable classification.

The server receives from each of one or more internet of things connected AEDs an ECG measurement, classifies each of the ECG measurements and transmits the classification back to the respective AED. Utilizing a server to classify ECG measurements allows more powerful hardware to used, as the size, power and cost constraints that limit the hardware found in AEDs do not apply to a dedicated server.

The SAA may comprise a neural network trained using a training algorithm configured to receive an array of training inputs and known outputs. The training inputs can include training ECG measurements and the known outputs can include a classification of the training ECG measurement. The classification of the ECG measurement can be either a shockable classification or a non-shockable classification.

SAAs comprising neural networks can be particularly effective at classifying ECG measurements.

The training ECG measurements can include ECG measurements received from the one more AEDs.

Using previously received ECG measurements can allow new neural networks to be trained using an ever growing training data set, improving the accuracy of the new neural networks. The new neural networks can be used to upgrade the SAA used by the server. In this way, the classifications performed by the server can be improved over time.

According to examples in accordance with an aspect of the invention, there is also provided a method of determining if a defibrillation shock should be administered. The method comprises:

collecting, by an automated external defibrillator, AED, an electrocardiogram, ECG, measurement of a heart;

transmitting, by the automated external defibrillator, the ECG measurement to a remote processing device;

receiving, by the AED from the remote processing device, a first classification of the ECG measurement, wherein the first classification is selected from a list comprising at least a shockable classification and a non-shockable classification;

determining, by the AED, a second classification of the ECG measurement before or after the transmitting of the ECG measurement, wherein the second classification is selected from a second list comprising at least a shockable classification and a non-shockable classification; and determining, at the AED, that a defibrillation shock is required if one or more of the first classification and the second classification of the ECG measurement is the shockable classification.

The method uses the AED to make an ECG measurement of a subject's heart and send the ECG measurement to a remote processing device. The AED subsequently receives from the remote processing device a first classification of the ECG measurement. The AED also determines, using a local SAA, a second classification of the ECG measurement. This determination step can happen before, at the same time as, or after the AED transmits the ECG measurement to the remote processing device. The AED determines, based on the first and second classifications, whether a defibrillation shock is required. If one of the first and second classifications are the shockable classification, the AED determines that a defibrillation shock is required. By using the AED to determine a second classification of the ECG measurement, and determining that a shock is required if one or more of the first and second classifications of the ECG measurement is shockable, the AED can operate independently of the remote processing device, if it is required. For example, if the AED is not able to connect to the remote processing device, it can still analyze the ECG measurement and determine whether a defibrillation shock is required.

The method may further comprise:

receiving, by the remote processing device, the ECG measurement;

determining, by the remote processing device, the first classification of the ECG measurement; and transmitting, by the remote processing device, the first classification of the ECG measurement to the AED.

The second list may further comprise an uncertain classification.

The ECG measurement may be transmitted to the remote processing device before or after the AED determines the second classification.

In examples in which the ECG measurement is transmitted to the remote processing device before the AED determines the second classification, the method minimizes the time between making the ECG measurement and receiving the first classification. This is particularly beneficial in cases where the second classification is uncertain or non-shockable, but the first classification is shockable. Where the second classification would not cause a defibrillation shock to be administered, but the first classification would cause a defibrillation shock to be administered, it is important that the first classification is received by the AED as soon as possible. This is because the first classification is more accurate than the second classification, and the sooner a defibrillation shock can be administered to the subject, the better their chances of survival.

Alternatively, the ECG measurement may be transmitted to the remote processing device after the AED determines the second classification.

In this way, the method can minimize the time between making the ECG measurement and determining the second classification. This is particularly beneficial in cases where the second classification is shockable, because it enables a defibrillation shock to be administered as quickly as possible. Often, it is quicker to determine the second classification than it is to transmit the ECG measurement to the remote processing device and wait to receive the first classification. For safety reasons, the AED is configured to administer a defibrillation shock if either the first or second classification is the shockable classification. Consequently, if the second classification is calculated more quickly than the first, and found to be shockable, it is determined that a defibrillation should be administered irrespective of the first classification, so the determination of the first classification is of less immediate importance.

The ECG measurement may only be transmitted to the remote processing device if the second classification is the non-shockable classification. Where the second list also comprises the uncertain classification, the ECG measurement may only be transmitted to the remote processing device if the second classification is the uncertain classification, or one of the uncertain classification and the non-shockable classification.

As noted above, if the second classification can be determined more quickly than the first, and if the second classification is the shockable classification, the AED can determine that a defibrillation shock is required based on the second classification alone. At this point, there is little immediate value in calculating the first classification. Rather, the benefits of the first classification are primarily provided in the case that the second classification is the uncertain or non-shockable classification. By transmitting the ECG measurement to the remote processing device when the second classification is the uncertain or non-shockable classifications, the benefits of the first classification can be provided without wasting resources (both in terms of the remote processing device's computational resources and the battery life of the AED) on simply confirming that a shockable second classification is correct.

The determination of the first classification by the remote processing device may include inputting the ECG measurement transmitted by the AED to a trained neural network. The neural network can be trained to analyze the ECG measurement and output the first classification of the ECG measurement.

The determining, at the AED, that a defibrillation shock is required, may comprise a first determining step based on whether the first classification is the shockable classification and performed at the time the AED receives the first classification; and a second determining step based on whether the second classification is the shockable classification and performed at the time the AED determines the second classification.

Where one of the first or second determining steps has determined that a defibrillation shock is required, the other determining step may not be performed.

Where the AED obtains the first and second classifications at the same time, the first determining step may be performed before the second determining step.

According to examples in accordance with an aspect of the invention, there is also provided a computer program comprising computer program code means which is adapted, when said program is run on processors of an automated external defibrillator, AED, and a server, to implement the method defined above.

According to examples in accordance with an aspect of the invention, there is also provided a defibrillator system comprising the automated external defibrillator and server defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
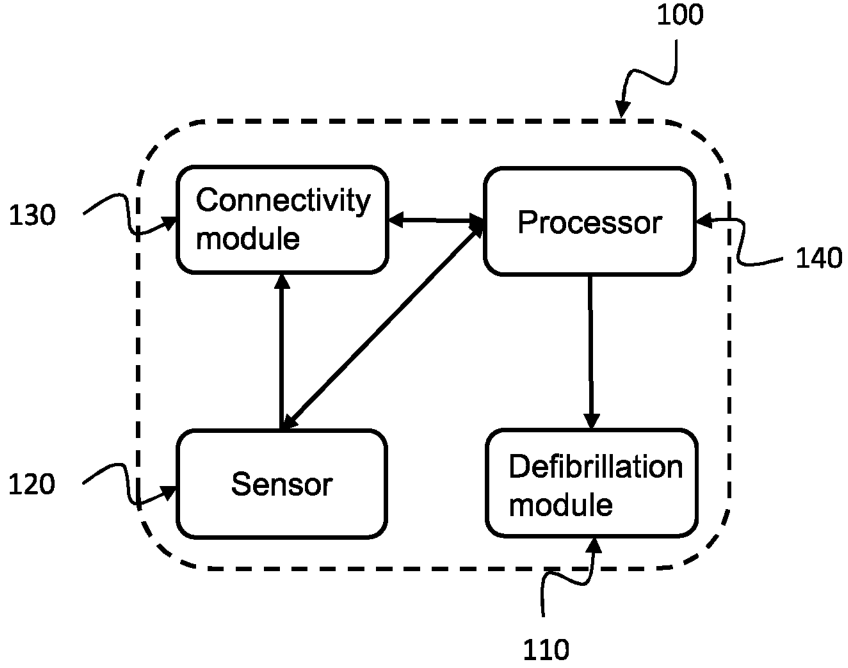
FIG. 1 shows an example of an automated external defibrillator.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an Automated External Defibrillator AED and a server. The AED makes an ECG measurement of a heart and transmits the measurement to a remote processing device, for example the server, and receives back from the server a first classification of the ECG measurement. The AED also performs a local analysis of the ECG measurement to determine a second classification of the ECG measurement. The AED determines whether to administer a shock/instruct a user to administer a shock based on the first and second classifications.

An exemplary AED will be described with reference to FIG. 1.

The AED 100 comprises a defibrillation module 110, a sensor 120, a connectivity module 130 and a processor 140. The defibrillation module 110 is able to administer a defibrillation shock. The sensor 120 makes an electrocardiogram (ECG) measurement of a heart. The connectivity module 130 communicates with a remote processing device (not shown in FIG. 1), for example a server, to transmit the ECG measurement made by the sensor to the remote processing device and to receive a first classification of the ECG measurement from the remote processing device. The first classification of the ECG measurement can be a shockable classification or a non-shockable classification. The processor 140 determines a second classification of the ECG measurement using a local shock advice algorithm SAA. The second classification can include a shockable classification, an uncertain classification and a non-shockable classification. If one or both of the first or second classifications of the ECG measurement are the shockable classification, the processor 140 either causes the defibrillation module 110 to administer a defibrillation shock, or instructs a user to administer a defibrillation shock using the defibrillation module 110.

Although the analysis performed by the AED 100 will not have as high a sensitivity or specificity as the analysis performed by the remote processing device, it is nonetheless useful for the AED 100 to be able to classify the ECG measurements. For example, it cannot be guaranteed that the AED 100 will always be able to connect to the remote processing device, either due to network failures or due to the environment—for example, in underground train stations where wireless signals from the surface are blocked. In such circumstances, it is important that the AED 100 is still able determine whether a defibrillation shock should be administered, even at a reduced accuracy. More generally, it is important that a defibrillation shock is administered as soon as possible, when it is required. In many cases it is quicker to analyse the ECG measurement using onboard hardware than the remote processor.

In some examples, the processor 140 may first obtain both the first and second classifications before determining whether to cause the defibrillation module 110 to administer a shock/instruct a user to administer a shock. In other examples, the processor 140 may consider each of the first and second classifications individually at the time that they obtained. For example, if the second classification is the non-shockable classification and is determined before the first classification, the processor 140 will determine that a shock is not required. Then, when the first classification is later obtained by the processor 140, it will again determine whether a defibrillation shock is required based on the first classification. The processor 140 may be configured such that, even if both classifications are the shockable classification, only one defibrillation shock is administered.

In some examples, the connectivity module 130 may transmit the ECG measurement to the remote processing device before the processor 140 determines the classification of, or begins to analyze, the ECG measurement. This reduces the time between making the ECG measurement and receiving the first classification of the ECG measurement. This is particularly valuable in cases where the subject has a borderline shockable heart rhythm. The limited analysis that the AED 100 is able to perform on the ECG measurement can, in many cases, classify borderline rhythms as non-shockable or uncertain when they are actually shockable rhythms. For such borderline heart rhythms, the superior sensitivity and specificity of the advanced SAAs utilized by the remote processing device are needed. By minimizing the time between making the ECG measurement and receiving the first classification from the remote processing device, a subject who requires a defibrillation but was incorrectly classified by the AED 100 as having a non-shockable or uncertain heart rhythm can receive a defibrillation shock as quickly as possible.

It can also be preferable to transmit the ECG measurement to the remote processing device before the AED 100 determines the second classification of the ECG measurement in situations where the AED 100 has a high speed connection with the remote processing device. With a high speed connection, it is possible that it will be quicker to transmit the ECG measurement to the remote processing device, wait for the remote processing device to analyze the ECG measurement and subsequently transmit the first classification back to the AED 100, than to analyze the ECG measurement using the local processor 140 in order to determine the second classification. In such cases, the AED 100 can more accurately and more quickly determine whether a defibrillation shock is required by relying on the first classification. However, it can be dangerous to rely solely on the remote processing device to classify the ECG measurement. No SAA or computer system is perfect, and occasionally the remote processing device may incorrectly classify a shockable heart rhythm as non-shockable. Furthermore, wireless signals can be inconsistent and the AED 100 and remote processing device may lose connection in an emergency. In such situations, by still using the processor 140 to determine the second classification, the local SAA may be able to correctly identify that the ECG measurement is shockable, and cause a defibrillation shock to be administered or a user to be instructed to administer a defibrillation shock.

In other examples, the processor 140 may first determine the classification of the ECG measurement before the connectivity module 130 transmits the ECG measurement to the remote processing device. This can reduce the time between making the ECG measurement and determining the second classification of the ECG measurement. This can be useful where the AED 100 has a weak or slow connection to the remote processing device, or where the processor 140 is sufficiently powerful/includes sufficiently powerful hardware to be able to determine the second classification more quickly than the time taken to transmit the ECG measurement to the remote processing device and to receive the first classification.

In some examples in which the AED 100 is configured to transmit the ECG measurement to the remote processing device after the processor 140 determine the second classification, the AED 100 may only transmit the ECG measurement if the second classification is the non-shockable classification. Alternatively, the AED 100 may only transmit the ECG measurement if the second classification is the uncertain classification, or optionally one of the uncertain classification and the non-shockable classification. Because the AED 100 is configured to administer a defibrillation shock when one of the first and second classifications is the shockable classification, there is no immediate medical benefit to having the remote processing device analyze an ECG measurement that has already been classified by the processor 140 as shockable. Resources of both the AED 100 and remote processing device (such as electrical power and computation time) can be saved by only transmitting ECG measurements to the remote processing device when the second classification of the ECG measurement is uncertain or non-shockable, as these are the situations where the remote processing device's analysis have immediate medical benefit.

The remote processing device may be a server, a computer, a mobile phone or any other device capable of being used to classify the ECG measurements.

Figure 2:
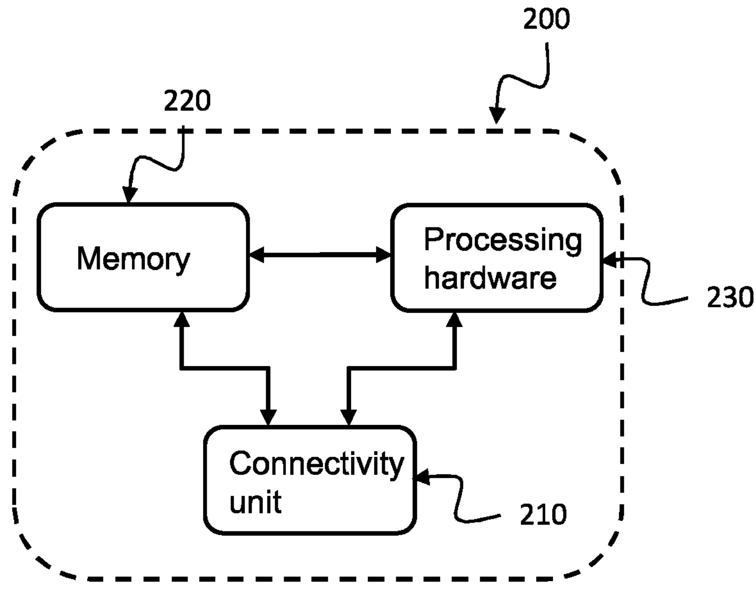
FIG. 2 shows an example of a server.

A second aspect of the invention provides a server for performing the remote ECG analysis, for example as shown in FIG. 2.

The server 200 comprises a connectivity unit 210, a memory 220 and processing hardware 230. The connectivity unit 210 communicates with the AED 100, receiving from the AED 100 an ECG measurement. The memory 220 stores a shock advice algorithm (SAA), used by processing hardware 230 to analyze the ECG measurement. The processing hardware 230 is configured to determine a first classification of the ECG measurement using the stored SAA. The first classification is selected from a list including at least a shockable classification and a non-shockable classification. The connectivity unit 210 transmits the first classification to an AED 100.

Figure 3:
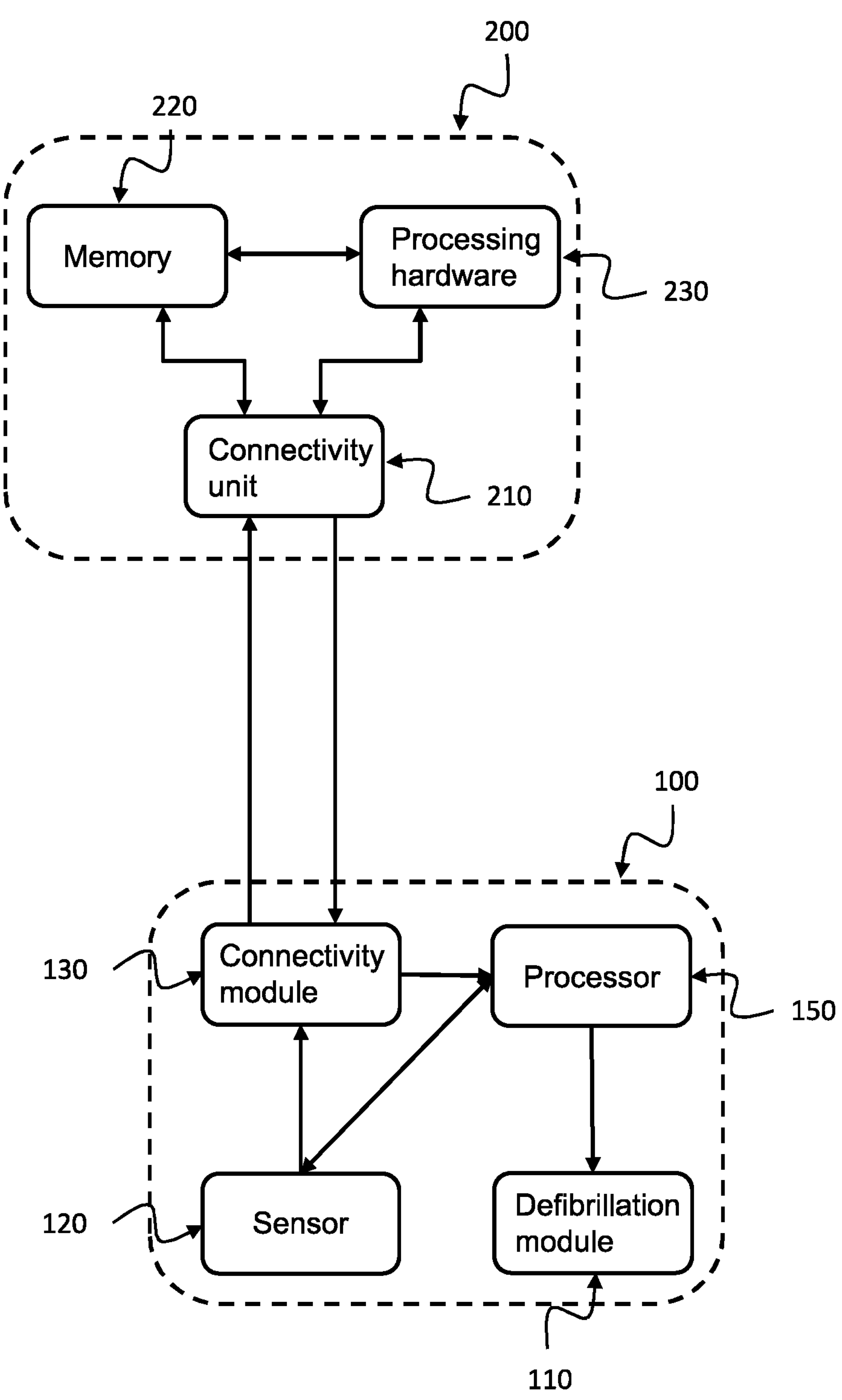
FIG. 3 shows an example of a defibrillator system.

One example of the communication between the AED 100 and Server 200 in a defibrillator system is depicted in FIG. 3. While the connectivity unit 210 and the connectivity module 130 are depicted as communicating directly, they may communicate via one or more other devices or intermediaries. The connectivity module 130 of the AED 100 and the connectivity unit 210 of the server 200 can communicate using Wifi or other wireless communication technologies, for example cell networks like 3G, 4G, 5G or NBIoT. In particular, 5G communication can be especially useful as it enables the fast transmission of data between the AED 100 and server 200, and is becoming increasingly common.

In some examples, the server 200 may serve a plurality of AEDs 100. The server 200 may receive from each one of a plurality of AEDs 100, an ECG measurement. The server 200 may analyze each ECG measurement to determine the first classification of said ECG measurement, and send the first classification to the respective AED 100. In other words, for each AED 100 served by the server 200, the server 200 can receive an ECG measurement from that AED 100, determine a first classification for that ECG measurement and transmit the first classification back to that AED 100.

In some examples, the server 200 can use a SAA that includes a neural network. The neural network may receive, as an input, the ECG measurement and output a first classification of the ECG measurement. The neural network may be trained using training ECG measurements that have been labelled with the correct classifications. The SAA used by the server 200 may be upgraded over time with improved neural networks. In particular, the ECG measurements received by the server 200 may be used in the training of a new neural network. Preferably, the server 200 can receive ECG measurements from multiple AEDs 100, increasing the amount of training data available to train new SAAs. The connectivity unit 210 can be used to receive upgraded SAAs, and the memory 220 can store the new upgraded SAA for use by the processing hardware 230.

The processing hardware 230 of the server 200 can comprise one or both of general purpose processing hardware (for example, a CPU), and fixed function hardware (such as a neural network accelerator). In examples in which the SAA includes a neural network, it can be particularly useful to process the neural network using fixed function hardware in order to reduce processing time.

A third aspect of the invention provides a method, for example as described with reference to FIG. 4.

In step 310, the AED 100 collects an ECG measurement of a heart. In step 320, the AED 100 transmits the ECG measurement to a remote processing device, optionally the server 200. In step 330, the AED 100 receives from the remote processing device a first classification of the ECG measurement. The first classification may be a shockable classification or a non-shockable classification. In step 340, the AED 100 determines a second classification of the ECG measurement. The second classification is selected from a second list comprising at least a shockable classification, an uncertain classification and a non-shockable classification. In step 350, the AED 100 determines that a defibrillation shock is required if one or more of the first and second classifications of the ECG measurement is the shockable classification.

Figure 5A:
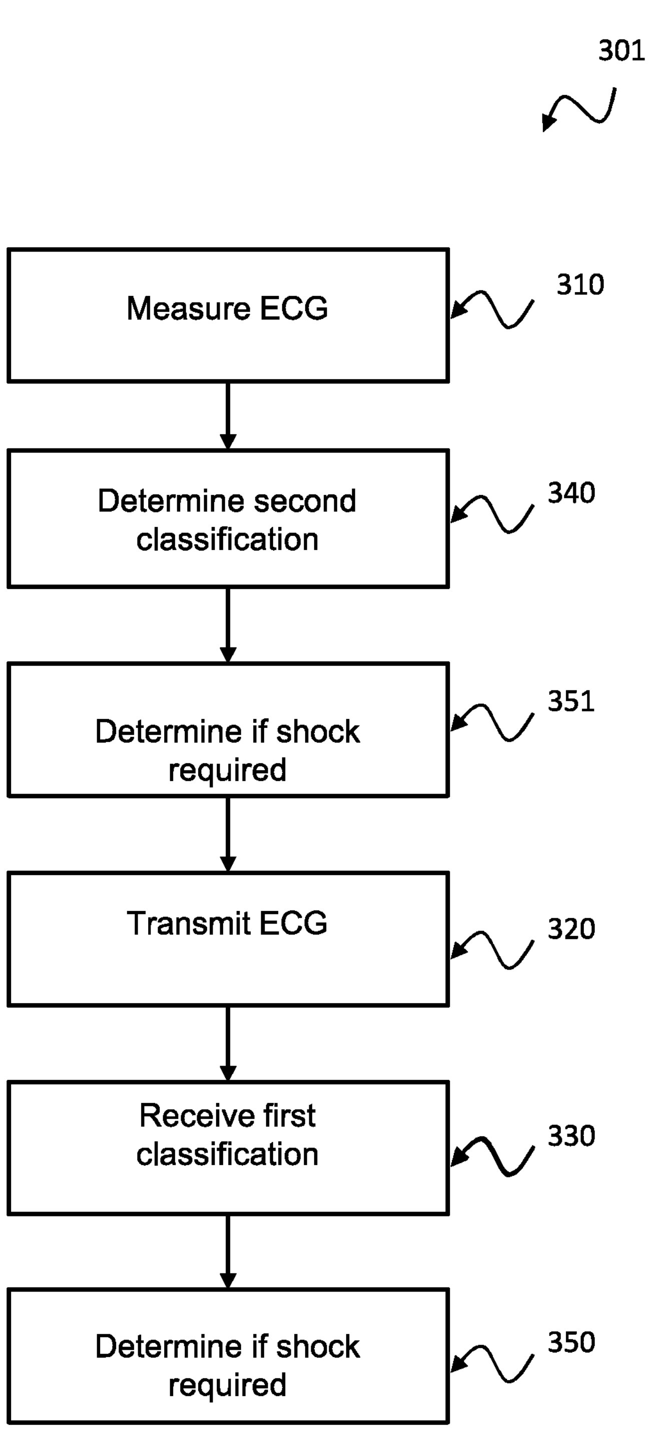
FIG. 5A is a flow diagram depicting a second exemplary method.

In some examples, the AED 100 may transmit 320 the ECG measurement to the remote processing device after the AED 100 determines 340 the second classification of the ECG measurement. FIG. 5A illustrates one such method 301, in which step 340 is performed before step 320. In addition to this, the AED 100 may determine 351 whether a shock is required based solely on the second classification and before the AED transmits 320 the ECG measurement to the remote processing device. The AED 100 may only transmit 320 the ECG measurement when the second classification is one of the non-shockable classification and the uncertain classification. In other words, the AED 100 may only transmit the 320 the ECG measurement if it determines 351, based on the second classification, that a shock is not required. In this example, the AED 100 performs a second determination step 350 based on the first classification to determine whether a shock is required.

Figure 5B:
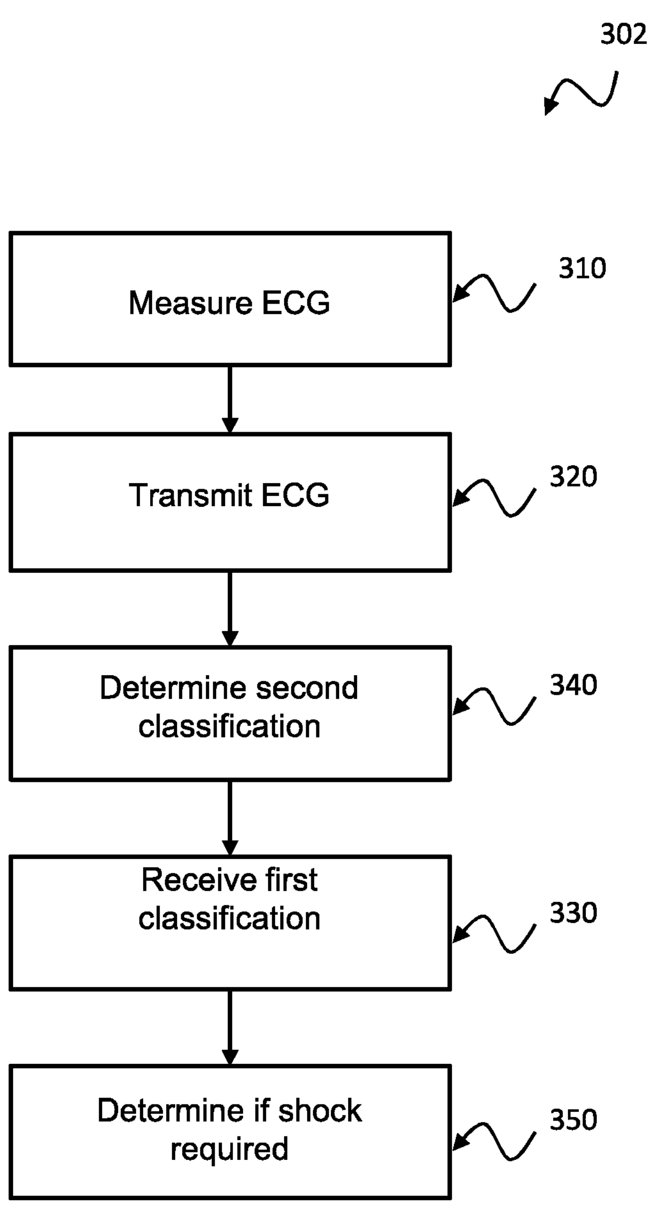
FIG. 5B is a flow diagram depicting a third exemplary method.

In other examples, such as the method 302 depicted in FIG. 5B, the AED may transmit 320 the ECG to the remote processing device, determine 340 the second classification of the ECG and then receive 330 the first classification of the ECG. In other words, the AED may perform step 320, then 340, then 330. The method may further include performing a determining step based on the second classification before step 330.

Figure 4:
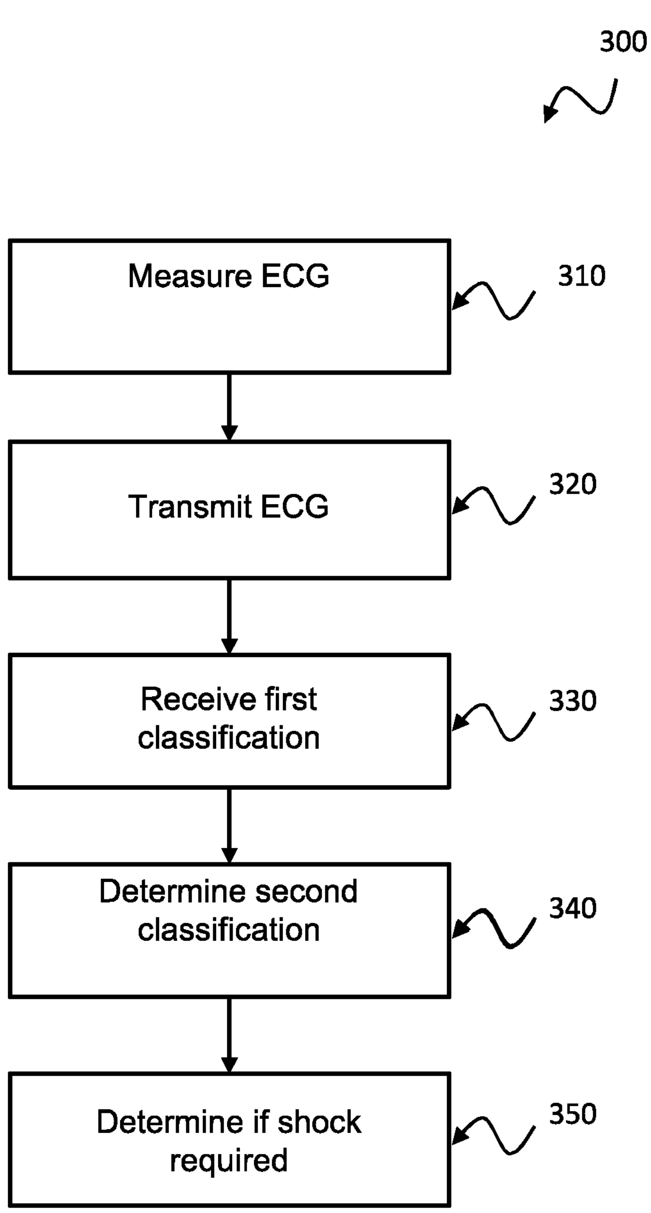
FIG. 4 is a flow diagram depicting an exemplary method.
Figure 6:
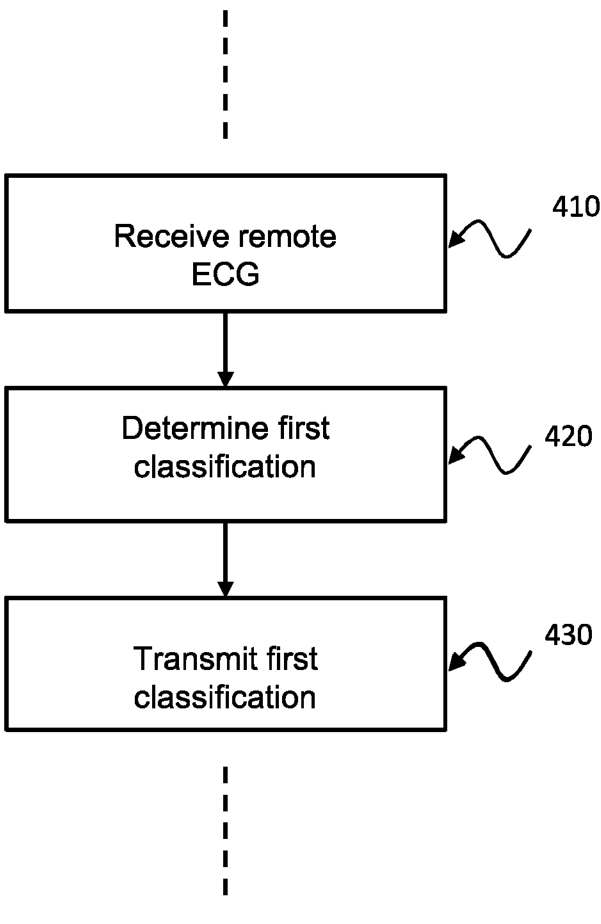
FIG. 6 is a flow diagram depicting part of a fourth exemplary method.

FIG. 6 illustrates additional method steps that may be performed in addition to the steps shown in FIGS. 4, 5A and 5B, and discussed above. In some examples, the method can further comprise the steps of receiving 410 the ECG measurement by a remote processing device; determining 420 the first classification of the ECG measurement by the remote processing device; and transmitting 430, by the remote processing device, the first classification to the AED 100. The determining 420 can comprise analyzing the ECG measurement using a neural network. The ECG measurement can be used as the input to the neural network, which may have been trained to output the first classification of the ECG measurement.

An "uncertain classification" is a classification for an ECG measurement that the SAA cannot classify as shockable or non-shockable. In many cases, this is because the hearth rhythm of the subject is borderline shockable, and the SAA used by the AED 100 is simply not advanced enough to properly classify it.

The remote processing device referenced in the various examples above may be the server 200, or may be a different device such as a computer or smartphone.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. An automated external defibrillator (AED), comprising:

a defibrillation module, structured and configured to administer a defibrillation shock;

a sensor structured and configured to make an electrocardiogram (ECG) measurement of a heart;

a connectivity module structured and configured to communicate with a remote processing device to transmit the ECG measurement and receive a first classification of the ECG measurement; and a processor comprising a memory structured and configured to store a local shock advice algorithm, the processor structured and configured to:

determine, using the local shock advice algorithm, a second classification of the ECG measurement, wherein the second classification is selected from a second list comprising at least a shockable classification and a non-shockable classification; and if at least one of the first classification and the second classification of the ECG measurement is a shockable classification, either:

cause the defibrillation module to administer the defibrillation shock; or advise a user to administer the defibrillation shock, wherein the connectivity module is structured and configured to transmit the ECG measurement to the remote processing device both before the processor determines the second classification of the ECG measurement and after the processor determines the second classification of the ECG measurement, and only when the determined second classification of the ECG measurement is not the shockable classification.

2. The AED of claim 1, wherein the second list further comprises an uncertain classification, and wherein the connectivity module is further structured and configured to transmit the ECG measurement to the remote processing device after the processor determines the second classification of the ECG measurement and only when the determined second classification is one of the uncertain classification and the non-shockable classification.

3. The AED of claim 1, wherein the connectivity module is structured and configured to communicate wirelessly with the remote processing device using at least one of:

Wifi; or a cell network.

4. A defibrillator system comprising a remote processing device and one or more automated external defibrillators, wherein the one or more automated external defibrillators comprises a defibrillation module, structured and configured to administer a defibrillation shock;

a sensor structured and configured to make an electrocardiogram (ECG) measurement of a heart;

a connectivity module structured and configured to communicate with the remote processing device to transmit the ECG measurement and receive a first classification of the ECG measurement; and a processor comprising a memory structured and configured to store a local shock advice algorithm, the processor structured and configured to:

determine, using the local shock advice algorithm, a second classification of the ECG measurement, wherein the second classification is selected from a second list comprising at least a shockable classification and a non-shockable classification; and if at least one of the first classification and the second classification of the ECG measurement is a shockable classification, either:

cause the defibrillation module to administer the defibrillation shock; or advise a user to administer the defibrillation shock, wherein the connectivity module is structured and configured to transmit the ECG measurement to the remote processing device both before the processor determines the second classification of the ECG measurement and after the processor determines the second classification of the ECG measurement, and only when the determined second classification of the ECG measurement is not the shockable classification, wherein the remote processing device comprises:

a connectivity unit structured and configured to:

receive, from each of the one or more automated external defibrillators, the ECG measurement; and transmit the first classification of the ECG measurement to the respective automated external defibrillator;

a memory structured and configured to store a remote processing device based shock advice algorithm; and processing hardware structured and configured to determine, using the remote processing device based shock advice algorithm, the first classification of the ECG measurement, wherein the first classification is selected from a first list comprising at least a shockable classification and a non-shockable classification.

5. The system of claim 4, wherein the remote processing device based shock advice algorithm comprises a neural network that is trained using a training algorithm configured to receive an array of training inputs and known outputs, wherein the training inputs comprise training ECG measurements and the known outputs comprise a classification of the training ECG measurements.

6. The system of claim 5, wherein the training ECG measurements comprise the ECG measurements received from the one or more automated external defibrillators and wherein the classification of the training ECG measurement is either the shockable classification or the non-shockable classification.

7. A non-transitory computer-readable medium having stored thereon a computer program comprising computer-executable instructions which, when executed by processors of an automated external defibrillator (AED), cause the processors to implement the following steps:

collecting, by the AED, an electrocardiogram (ECG) measurement of a heart;

transmitting, by the AED, the ECG measurement to a remote processing device;

receiving, by the AED from the remote processing device, a first classification of the ECG measurement, wherein the first classification is selected from a first list comprising at least a shockable classification and a non-shockable classification;

determining by the AED, a second classification of the ECG measurement before or after the transmitting of the ECG measurement, wherein the second classification is selected from a second list comprising at least a shockable classification and a non-shockable classification; and determining, at the AED, that a defibrillation shock is required if one or more of the first classification and the second classification of the ECG measurement is the shockable classification, and causing a defibrillation module of the AED to administer the defibrillation shock; or to advise a user to administer the defibrillation shock, wherein the steps of transmitting and receiving are implemented only when the second classification of the ECG measurement is not the shockable classification, and wherein the transmitting step is implementable both before and after the step of determining the second classification of the ECG measurement.

8. The computer program of claim 7, wherein the second list further comprises an uncertain classification, and wherein the ECG measurement is transmitted to the remote processing device only if the second classification is one of the uncertain classification and the non-shockable classification.

* * * * *